United States Patent [19]

McQuinn et al.

[11] Patent Number: 4,496,734

[45] Date of Patent: Jan. 29, 1985

[54] METABOLITE

[75] Inventors: Roy L. McQuinn, White Bear Lake; William R. Bronn, Maplewood; Elden H. Banitt, Woodbury, all of Minn.

[73] Assignee: Riker Laboratories, Inc., St. Paul, Minn.

[21] Appl. No.: 551,966

[22] Filed: Nov. 15, 1983

[51] Int. Cl.$^3$ ............................................. C07D 211/76
[52] U.S. Cl. ..................................................... 546/221
[58] Field of Search .......................................... 546/221

[56] References Cited

U.S. PATENT DOCUMENTS

| | | | |
|---|---|---|---|
| 3,655,728 | 4/1972 | Mendel | 260/473 R |
| 3,719,687 | 3/1973 | Mendel | 260/326.3 |
| 3,900,481 | 8/1975 | Banitt | 260/293.77 |
| 4,071,524 | 1/1978 | Banitt | 260/293.77 |
| 4,097,481 | 6/1978 | Banitt | 260/293.77 |
| 4,339,587 | 7/1982 | Banitt | 546/337 |

OTHER PUBLICATIONS

E. H. Banitt et al., Journal of Medicinal Chemistry, 20, 821–826, (1977).

*Primary Examiner*—Norma S. Milestone
*Attorney, Agent, or Firm*—Donald M. Sell; James A. Smith; Robert W. Sprague

[57] ABSTRACT

Synthetic 5-hydroxy-N-(6-oxo-2-piperidylmethyl)-2-(2,2,2-trifluoroethoxy) benzamide. The compound 5-hydroxy-N-(6-oxo-2-piperidylmethyl)-2-(2,2,2-trifluoroethoxy) benzamide is a metabolite of the antiarrhythmic agent 2,5-bis(2,2,2-trifluoroethoxy)-N-(2-piperidylmethyl)-benzamide.

2 Claims, No Drawings

METABOLITE

TECHNICAL FIELD

This invention relates to a metabolite of an antiarrhythmic agent which is a N-(piperidylmethyl)benzamide.

BACKGROUND OF THE INVENTION

Esters of benzoic acid which are substituted on the aromatic ring by 1,1-dihydroperfluoroalkoxy substituents and exhibit anesthetic activity are described in U.S. Pat. No. 3,655,728. Amides of benzoic acid which are substituted on the aromatic ring by 1,1-dihydroperfluoroalkoxy substituents and exhibit antiarrhythmic activity are described in U.S. Pat. No. 3,719,687. U.S. Pat. Nos. 3,900,481, 4,071,524 and 4,097,481 describe antiarrhythmic agents including, inter alia, N-(piperidylmethyl)benzamides substituted by one or more 1,1-dihydroperfluoroalkoxy groups. Above-mentioned U.S. Pat. No. 3,900,481 discloses the compound 2,5-bis(2,2,2-trifluoroethoxy)-N-(2-piperidylmethyl)-benzamide, a particularly useful antiarrhythmic agent also known as flecainide. An article appearing in the Journal of Medicinal Chemistry, 20, 821 (1977) discloses many of the compounds of the patents and also discloses various additional compounds such as 2-(2,2,2-trifluoroethoxy)-N-(2-piperidylmethyl)benzamides in which the aromatic ring is substituted in the 5-position by a non-functional group, i.e., methyl, chloro or fluoro.

U.S. Pat. No. 4,339,587 discloses 5-hydroxy-2-(2,2,2-trifluoroethoxy)-N-(2-piperidylmethyl)-benzamide and synthetic intermediates useful in the synthesis thereof. This compound is a metabolite of flecainide and is useful as an intermediate in the synthesis of flecainide and as an antiarrhythmic agent itself.

DETAILED DESCRIPTION OF THE INVENTION

This invention relates to synthetic 5-hydroxy-N-(6-oxo-2-piperidylmethyl)-2-(2,2,2-trifluoroethoxy)benzamide of the formula I

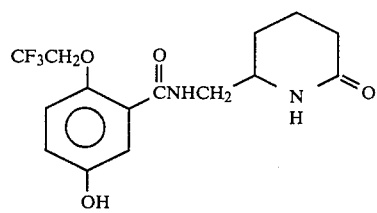

The compound 5-hydroxy-N-(6-oxo-2-piperidylmethyl)-2-(2,2,2-trifluoroethoxy)benzamide is a metabolite of flecainide in certain mammals.

Synthetic 5-hydroxy-N-(6-oxo-2-piperidylmethyl)-2-(2,2,2-trifluoroethoxy)benzamide is useful for studying the metabolism of flecainide in mammals.

The following Reaction Scheme A shows one synthetic route by which the compound 5-hydroxy-N-(6-oxo-2-piperidylmethyl)-2-(2,2,2-trifluoroethoxy)benzamide may be prepared:

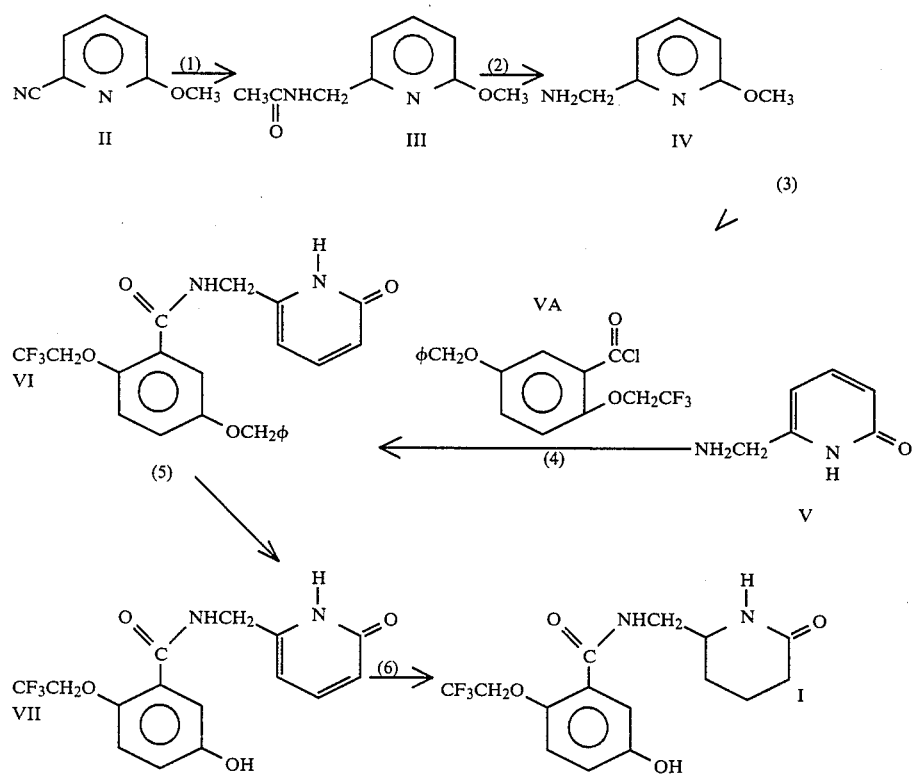

In step (1) the known compound 2-cyano-6-methoxypyridine (Formula II) is reductively acetylated to provide the novel compound of Formula III. The reductive acetylation is carried out catalytically in the presence of hydrogen gas and Raney nickel catalyst. An acetate salt such as sodium acetate is required, preferably in 0.1 to 1.0 molar amounts relative to the compound of Formula II. A large excess of acetic anhydride is used. The reaction occurs readily at moderate (0° to 50° C.) temperatures.

The compound of Formula III is deacetylated by conventional acid hydrolysis techniques in step (2) to provide novel 2-aminomethyl-6-methoxypyridine (Formula IV). It has been found that dilute aqueous hydrochloric acid accomplishes this reaction readily with simple refluxing. The compound is obtained as a hydrochloride addition salt.

In step (3) the 2-aminomethyl-6-methoxypyridine of Formula IV is converted to novel 6-aminomethyl-2(1H)-pyridone (Formula V). This conversion is somewhat slower than the deacetylation of step (2), but it occurs readily also. Indeed, the reaction conditions of step (2), if carried out for several hours, were found to partially achieve the reaction of step (3). Step (3) was completed by heating and refluxing the compound of Formula IV (or a mixture of III and IV) in 48% hydrobromic acid. The product is obtained as a hydrobromide addition salt.

as sodium carbonate. The product of step (4) is novel 6-[5-benzyloxy-2-(2,2,2-trifluoroethoxy)benzamidomethyl]-2(1H)-pyridone (Formula VI).

The compound of Formula VI is converted as shown in step (5) to novel 6-[5-hydroxy-2-(2,2,2-trifluoroethoxy)benzamidomethyl]-2(1H)-pyridone (Formula VII) by catalytic reduction on a Parr apparatus at about 20° C. The catalyst used is palladium on charcoal. The reduction is carried out in an inert solvent such as a lower alkanol, for example, ethanol and/or methanol.

In step (6), the compound of Formula VII is reduced to provide 5-hydroxy-(6-oxo-2-piperidylmethyl)-2-(2,2,2-trifluoroethoxy)benzamide of the invention. This reduction is readily accomplished in the presence of hydrogen gas using rhodium on alumina as catalyst. The reduction occurs rapidly at 20° C. in a nonreactive solvent such as a lower alkanol, for example, ethanol and/or methanol.

The following Reaction Scheme B illustrates an alternative synthetic route by which 5-hydroxy-N-(6-oxo-2-piperidylmethyl)-2-(2,2,2-trifluoroethoxy)benzamide of the invention may be prepared:

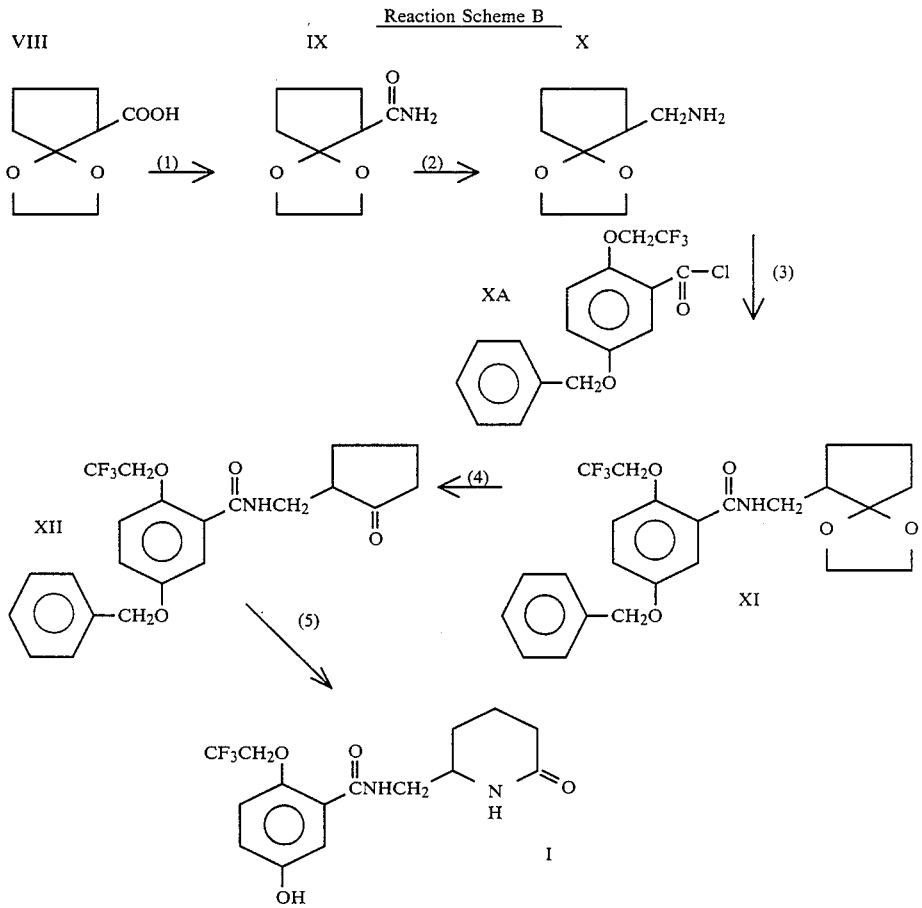

Step (4) involves the reaction of 6-aminomethyl-2(1H)-pyridone (Formula V) with 5-benzyloxy-2-(2,2,2-trifluoroethoxy)benzoyl chloride (Formula VA), a compound described in U.S. Pat. No. 4,339,587. This reaction can also be carried out between 6-aminomethyl-2(1H)-pyridone and the known compound, 2,5-bis(2,2,2-trifluoroethoxy)benzoyl chloride. This reaction may be carried out in an inert solvent such as acetone with (preferably) or without an acid acceptor such In step (1), known 2-oxocyclopentanecarboxylic acid ethylene ketal (Formula VIII) is converted to 2-oxocyclopentanecarboxamide ethylene ketal (Formula IX) under anhydrous conditions using a conventional mixed anhydride method. More particularly, the reactant is dissolved in a suitable inert solvent such as chloroform in the presence of an organic acid acceptor such as an organic amine (e.g., triethylamine) or an inorganic acid acceptor such as sodium carbonate or sodium bicarbonate. Ethyl chloroformate or an equivalent reactive blocking agent is added to the mixture, followed by the addition of anhydrous ammonia to provide the amide of Formula IX.

Alternatively, a simple ester of the compound of Formula VIII may be reacted with alcoholic ammonia by heating in a bomb to provide the amide of Formula IX.

The amide of Formula IX is readily reduced in step (2) using a metal hydride reducing agent such as lithium aluminum hydride to provide (2-oxocyclopentane)-methylamine ethylene ketal (Formula X) which may be readily converted to the amine salt by conventional methods.

In step (3) the amine of Formula X is reacted with known 5-benzyloxy-2-(2,2,2-trifluoroethoxy)benzoyl chloride (Formula XA) by heating in an inert solvent in the presence of an organic or inorganic acid acceptor such as those described above in connection with step (1). The product of step (3) is 5-benzyloxy-N-(2-oxocyclopentane)-methyl ethylene ketal-2-(2,2,2-trifluoroethoxy)benzamide (Formula XI).

In step (4) the benzamide of Formula XI is converted by hydrolysis to 5-benzyloxy-N-(2-oxocyclopentane)-methyl-2-(2,2,2-trifluoroethoxy)benzamide (Formula XII) by heating in an aqueous alcohol such as aqueous ethanol in the presence of dilute strong acid such as hydrochloric acid.

In step (5) the benzamide of Formula XII is reacted in a conventional Schmidt-type reaction by reacting with hydrazoic acid in the presence of sulfuric acid in an inert solvent or solvent blend such as a chloroform and benzene mixture. The product of step (5) is 5-hydroxy-N-(6-oxo-2-piperidylmethyl)-2-(2,2,2-trifluoroethoxy)-benzamide of the invention.

The following examples illustrate the preparation of the compound of the invention.

EXAMPLE 1

Preparation of Compound of Formula I By Reaction Scheme A

Part A. Preparation of 2-Acetamidomethyl-6-methoxypyridine

A mixture of 1.0 g (7.46 mmole) of 2-cyano-6-methoxypyridine, 0.37 g (4.48 mmole) of sodium acetate, 25 ml of acetic anhydride and about 1.0 g of Raney nickel was hydrogenated on a Paar apparatus for about 5.5 hours. The mixture was filtered, and then evaporated with warming in vacuo to provide 2-acetamidomethyl-6-methoxypyridine. The structural assignment was supported by infrared spectral analysis.

Part B. Preparation of 2-Aminomethyl-6-methoxypyridine

The crude product, 2-acetamidomethyl-6-methoxypyridine from Part A, was combined with 10 ml of 6N hydrochloric acid, and the resulting mixture was heated at its reflux temperature for about 16 hours. The mixture was evaporated to provide a tan solid residue. The product was determined by infrared and nuclear magnetic resonance spectral analyses to be a mixture of 2-aminomethyl-6-methoxypyridine hydrochloride and 6-aminomethyl-2(1H)-pyridone hydrochloride.

Part C. Preparation of 6-Aminomethyl-2(1H)-pyridone

The crude product from Part B was combined with 10 ml of 48% hydrobromic acid, and the resulting mixture was heated at its reflux temperature for one hour. Evaporation to dryness provided 6-aminomethyl-2(1H)-pyridone hydrobromide as a water-soluble solid. The structural assignment was supported by infrared and nuclear magnetic resonance spectral analyses.

Part D. Preparation of 6-[5-Benzyloxy-2-(2,2,2-trifluoroethoxy)benzamidomethyl]-2(1H)-pyridone To a stirred mixture of the crude product from Part C, 20 ml of acetone and 4.7 g of sodium carbonate was added dropwise 2.8 g (8.21 mmole) of 5-benzyloxy-2-(2,2,2-trifluoroethoxy)benzoyl chloride in 10 ml of acetone. The mixture was stirred at about 20° C. for about 16 hours. To the mixture was added 50 ml of acetone, and the resulting inorganic residue was separated by filtration and washed with acetone. The filtrate and washings were combined and evaporated. This residue was dissolved in benzene, and the solution was washed sequentially with 10% aqueous sodium carbonate solution, 2% acetic acid, water, saturated aqueous sodium bicarbonate solution and saturated aqueous sodium chloride solution. The organic solution was dried over magnesium sulfate, and then filtered and evaporated. The residue was boiled in carbon tetrachloride, and the mixture was cooled and the solid was separated by filtration. The solid was purified by chromatography on 30 g of silica gel. The column was eluted sequentially with 5% ethyl acetate in dichloromethane and 2% methanol in dichloromethane. The product was obtained as a white solid, 6-[5-benzyloxy-2-(2,2,2-trifluoroethoxy)benzamidomethyl]-2(1H)-pyridone. The structural assignment was supported by infrared and nuclear magnetic resonance spectral analyses.

Part E. Preparation of 6-[5-Hydroxy-2-(2,2,2-trifluoroethoxy)benzamidomethyl]-2(1H)-pyridone A mixture of 0.5 g of 6-[5-benzyloxy-2-(2,2,2-trifluoroethoxy)benzamidomethyl]-2(1H)-pyridone, 60 ml of ethanol, 40 ml of methanol and 0.043 g of 10% palladium on charcoal was hydrogenated on a Parr apparatus at about 20° C. for about 16 hours. Filtration followed by evaporation of the filtrate provided a residue which was triturated with acetonitrile. The solid was separated by filtration and washed with acetonitrile to provide 6-[5-hydroxy-2-(2,2,2-trifluoroethoxy)benzamidomethyl]-2(1H)-pyridone. The structural assignment was supported by infrared and nuclear magnetic resonance spectral analyses.

Part F. Preparation of 5-Hydroxy-N-(6-oxo-2-piperidyl)-methyl)-2-(2,2,2-trifluoroethoxy)benzamide A mixture of 0.16 g (0.468 mmole) of 6-[5-hydroxy-2-(2,2,2-trifluoroethoxy)benzamidomethyl]-2(1H)-pyridone, 0.05 g of 5% rhodium on alumina and 50 ml of methanol was hydrogenated on a Parr apparatus for 50 minutes. The mixture was filtered, the filtrate was evaporated, and the residue was dried to provide 5-hydroxy-N-(6-oxo-2-piperidylmethyl)-2-(2,2,2-trifluoroethoxy)-benzamide.

EXAMPLE 2

Preparation of the Compound of Formula I by Reaction Scheme B

Part A. Preparation of 2-Oxocyclopentanecarboxamide Ethylene Ketal

To a solution of about 65 g of ammonia in 200 ml of methanol was added 20 g (0.10 mole) of ethyl 2-oxocyclopentanecarboxylate ethylene ketal. The mixture was heated at 130° C. while shaking in a bomb for about 16 hours. The mixture was then filtered and the solid residue discarded. The filtrate was evaporated, the resulting residue triturated with hexane, and the solid separated by filtration. The solid was dissolved in chloroform and passed through a chromatography column of florisil to provide 3.5 g of white solid after removal of solvent. This solid was recrystallized from toluene to provide fine white needles of 2-oxocyclopentanecarboxamide ethylene ketal, m.p. 134–136. Analysis: Calculated for $C_8H_{13}NO_3$:%C, 56.1; %H, 7.65; %N,8.2; Found: %C, 56.2; %H, 7.6; %N, 8.2.

Part A'. Alternative Preparation of 2-Oxocyclopentanecarboxamide Ethylene Ketal To a stirred, cold (0° C.) solution of 1.72 g (0.01 mole) of 2-oxocyclopentanecarboxylic acid ethylene ketal in 35 ml of chloroform was added first 1.11 g (0.011 mole) of triethylamine and then 1.085 g (0.01 mole) of ethyl chloroformate, the latter being added in dropwise fashion. After stirring for 30 minutes, dry ammonia gas was bubbled in over about 5 minutes. A white solid separated while the mixture was stirred at about 0° C. for 30 minutes. The solid was separated by filtration and washed with chloroform, and the combined washings and filtrate were evaporated to provide a white solid residue of 2-oxocyclopentane-carboxamide ethylene ketal. Infrared spectral analysis showed the product to be identical to that obtained in Part A.

Part B. Preparation of (2-Oxocyclopentane)methylamine Ethylene Ketal

To a stirred suspension of 8.11 g (0.218 mole) of lithium aluminum hydride in 50 ml of diethyl ether under nitrogen was added, in small portions, 24.3 g (0.142 mole) of 2-oxocyclopentanecarboxamide ethylene ketal. The stirred mixture was heated at reflux for about one day, and the excess lithium aluminum hydride was then decomposed by adding sequentially and dropwise 8 ml of water, 12 ml of 10 percent aqueous sodium hydroxide solution, and an additional 20 ml of water. Filtration of the mixture followed by evaporation of the filtrate provided an oil. The oil was distilled to provide a clear, colorless liquid, b.p. 62°–65° C./0.4 mm of Hg, this being (2-oxocyclopentane)methylamine ethylene ketal.

To a solution of 0.5 g of the ketal in 50 ml of diethyl ether was added diethyl ether which had previously been saturated with hydrogen chloride until the mixture was acid to litmus paper. The solid was separated by filtration, washed with ether and recrystallized from acetonitrile to provide white solid (2-oxocyclopentane)methylamine ethylene ketal hydrochloride, m.p. 144°–146° C. Analysis: Calculated for $C_8H_{15}NO_2.HCl$:%C, 49.6; %H, 8.3; %N, 7.2; Found: %C, 49.4; %H, 8.4; %N, 7.1.

Part C. Preparation of 5-Benzyloxy-N-[(2-oxocyclopentane)methyl ethylene ketal]-2-(2,2,2-trifluoroethoxy)benzamide To a stirred suspension of 8.7 g (0.055 mole) of (2-oxocyclopentane)methylamine ethylene ketal, 17.6 g (0.166 mole) of sodium carbonate and 200 ml of benzene was added dropwise a solution of 19.1 g (0.0553 mole) of 5-benzyloxy-2-(2,2,2-trifluoroethoxy)benzoyl chloride in 100 ml of benzene. The mixture was then heated to reflux and maintained at reflux for one hour. The mixture was evaporated, and water and diethyl ether were added to the residue. The layers were separated, and the organic layer was washed with saturated sodium chloride solution and dried over magnesium sulfate. The organic layer was evaporated to provide an off-white residue. Recrystallization of a sample of the solid residue from 2:1 heptane:benzene with treatment with decolorizing charcoal provided 5-benzyloxy-N-[(2-oxocyclopentane)methyl ethylene ketal]-2-(2,2,2-trifluoroethoxy)benzamide, m.p. 81.5°–82.5° C. Analysis: Calculated for $C_{24}H_{36}F_3NO_5$:%C, 61.9; %H, 5.6; %N, 3.0; Found: %C, 61.9; %H, 5.6; %N, 2.8.

Part D. Preparation of 5-Benzyloxy-N-(2-oxocyclopentane)methyl-2-(2,2,2-trifluoroethoxy)benzamide To a solution of 24.3 g (0.0522 mole) of 5-benzyloxy-N-[(2-oxocyclopentane)methyl ethylene ketal]-2-(2,2,2-trifluoroethoxy)benzamide in 300 ml of ethanol was added 4 ml of 3N hydrochloric acid and 300 ml of water. The mixture was gradually heated to its reflux temperature and maintained at reflux for one hour. This mixture was cooled, 100 ml of water was added thereto, and the mixture was cooled with an ice bath. The white solid was separated by filtration and washed with cold water. A sample was recrystallized from 1:1 heptane-toluene to provide 5-benzyloxy-N-(2-oxocyclopentane)methyl-2-(2,2,2-trifluoroethoxy)benzamide, m.p. 105°–107° C. Analysis: Calculated for $C_{22}H_{22}F_3NO_4$: %C, 62.7; %H, 5.3; %N, 3.3; Found: %C, 62.7; %H, 5.3; %N, 3.1.

Part E. Preparation of the Compound of Formula I

To a stirred, chilled (0° C.) solution of 10 ml of concentrated sulfuric acid in 120 ml of chloroform was added dropwise a solution of 15.5 g (0.0368 mole) of 5-benzyloxy-N-(2-oxocyclopentane)methyl-2-(2,2,2-trifluoroethoxy)benzamide in 40 ml of chloroform and 28 ml of a 4 molar stock solution of hydrazoic acid in toluene. Stirring was continued for 1.5 hours at 0° C. after the completion of the addition. Water (100 ml) was added to the solution, and the organic layer was separated and dried over magnesium sulfate, and then evaporated. The residue was triturated with hot toluene, and cooled. The solid was separated by filtration, recrystallized from ethyl acetate with treatment with decolorizing charcoal and cooled to provide 5-hydroxy-N-(6-oxo-2-piperidylmethyl)-2-(2,2,2-trifluoroethoxy)benzamide, m.p. 156°–158° C. Analysis: Calculated for $C_{15}H_{17}F_3N_2O_4$: %C, 52.0; %H, 4.95; %N, 8.1; Found; %C, 51.5; %H, 5.1; %N, 7.7.

What is claimed is:

1. Synthetic 5-hydroxy-N-(6-oxo-2-piperidylmethyl)-2-(2,2,2-trifluoroethoxy)benzamide.

2. Substantially pure 5-hydroxy-N-(6-oxo-2-piperidylmethyl)-2-(2,2,2-trifluoroethoxy)benzamide.

* * * * *